US008850875B2

(12) United States Patent
Gentile et al.

(10) Patent No.: US 8,850,875 B2
(45) Date of Patent: Oct. 7, 2014

(54) SOOT BENCH TEST

(75) Inventors: Mitchell Gentile, Chesterland, OH (US); Matthew D. Gieselman, Wickliffe, OH (US); Matthew Henley, Wickliffe, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 315 days.

(21) Appl. No.: 13/534,311

(22) Filed: Jun. 27, 2012

(65) Prior Publication Data

US 2013/0008239 A1    Jan. 10, 2013

Related U.S. Application Data

(60) Provisional application No. 61/505,242, filed on Jul. 7, 2011.

(51) Int. Cl.
*G01N 30/90* (2006.01)
*G01N 13/00* (2006.01)
*G01N 33/30* (2006.01)

(52) U.S. Cl.
CPC ...................................... *G01N 33/30* (2013.01)
USPC ......................................... 73/61.54; 73/61.55

(58) Field of Classification Search
CPC .................................................... G01N 33/30
USPC .................................. 73/61.52, 61.54, 61.55
See application file for complete search history.

(56) References Cited

U.S. PATENT DOCUMENTS

| 5,370,805 A | 12/1994 | Smrcka et al. |
| 7,534,747 B2 | 5/2009 | Burrington et al. |
| 2009/0312205 A1* | 12/2009 | Colbourne et al. ........... 508/110 |
| 2012/0046206 A1 | 2/2012 | Gieselman et al. |

FOREIGN PATENT DOCUMENTS

| EP | 1959003 | 8/2008 |
| WO | 2008/086185 | 7/2008 |
| WO | 2010/099136 | 9/2010 |

* cited by examiner

*Primary Examiner* — Hezron E Williams
*Assistant Examiner* — David Z Huang
(74) *Attorney, Agent, or Firm* — David M. Shold, Esq.; Michael F. Esposito, Esq.

(57) ABSTRACT

The dispersibility of soot in a lubricant formulation containing a dispersant is evaluated by (a) preparing a dispersion of carbon black in the lubricant formulation; (b) depositing a sample of the dispersed carbon black from step (a) onto a planar chromatography medium; (c) subjecting the sample of (b) to chromatographic conditions and (d) evaluating the extent of migration of the carbon black by comparing the density of darkening due to carbon black at pre-defined locations along the chromatography medium. The liquid mobile chromatography phase comprises a mixture of a liquid non-aromatic hydrocarbon portion having viscosity and boiling point less than that of an oil of lubricating viscosity; and an oil component comprising an oil of lubricating viscosity and the dispersant or dispersants that are also contained within the lubricant formulation.

16 Claims, 1 Drawing Sheet

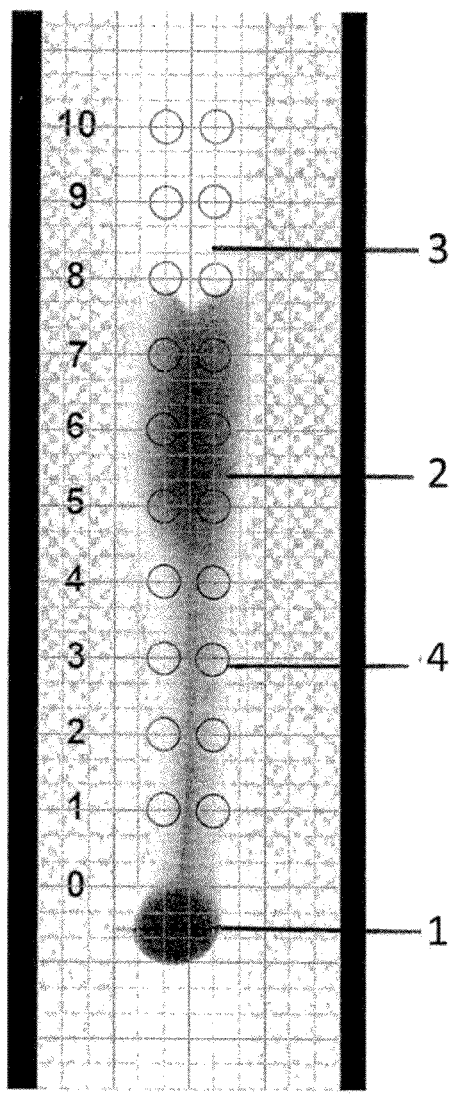

US 8,850,875 B2

SOOT BENCH TEST

BACKGROUND OF THE INVENTION

The disclosed technology relates to an improved method for evaluating the effect of soot on lubricant oils, on a bench scale test.

Modern heavy diesel (HD) engine oils must have sufficient dispersancy to keep soot (a product of the incomplete combustion of diesel fuel) suspended in the bulk oil. Various API engine oil categories require minimum soot dispersion performance as measured by fired engine tests. For example, API CH-4 and CI-4 oils must exhibit good soot dispersion in the Mack T8E engine test. Such fired engine tests are lengthy and expensive. For instance, modern HD engine oil soot dispersion tests such as the Mack T8E and Mack T11 require as long as 2 weeks to complete and cost as much as 80,000 USD. A formulator may need to screen dozens of formulas in order to find one with acceptable performance.

An efficient, easy, and short screening method for predicting the performance of oils in sooted engine tests is highly desirable. Such a screen test is described herein. The current invention gives the HD formulator a tool to perform such screening in an efficient and inexpensive manner. The new test described here has better predictive ability and is more visually impactful than earlier soot screen tests. The new inventive screen test correctly predicts engine test performance of API CH-4 oils while older screen tests do not. The screen test described here is a blotter strip test and is an improvement on earlier blotter spot tests as described, for instance, in WO2010/099136, Sep. 2, 2010, Gieselman et al.; see for instance paragraph 0137.

Older soot dispersion tests are sometimes run in the blotter spot mode. While the test is appropriate for showing the difference in performance between very poor oil and top tier oils, it is not appropriate for distinguishing between oils with finer differences in performance. Another advantage of the disclosed test is that it can distinguish in a statistically significant way between fair performing oils and good performing oils.

SUMMARY OF THE INVENTION

The disclosed technology provides a method for evaluating the dispersibility of soot in a lubricant formulation which comprises at least one dispersant, comprising the steps of:

(a) preparing a dispersion of carbon black in the lubricant formulation;

(b) depositing a sample of the dispersed carbon black from step (a) onto a planar chromatography medium;

(c) subjecting the sample of (b) to chromatographic conditions comprising introducing a liquid mobile phase to one side of said sample and permitting the liquid mobile phase to migrate past the sample of (b), thereby causing at least a portion of said carbon black to migrate in the direction of the migration of the liquid mobile phase; and (d) evaluating the extent of migration of said carbon black by comparing the density of darkening due to carbon black at pre-defined locations along the chromatography medium;

wherein said liquid mobile phase comprises a mixture of:

(i) a liquid hydrocarbon portion comprising a hydrocarbon having viscosity and boiling point less than that of an oil of lubricating viscosity (e.g., less than that of the oil of lubricating viscosity employed in part (ii) below); and (ii) an oil component (such as a lubricating oil) comprising an oil of lubricating viscosity and the dispersant or dispersants contained within the lubricant formulation.

BRIEF DESCRIPTION OF THE FIGURE

FIG. 1 shows a chromatographic strip as developed by the present process, along with an analytical grid superimposed thereon.

DETAILED DESCRIPTION OF THE INVENTION

Various preferred features and embodiments will be described below by way of non-limiting illustration.

The test of this invention is a blotter strip test run in a thin-layer chromatography (TLC) mode. Briefly, a candidate oil is prepared by suspending a carbon black sample, which serves as a model for soot (hereinafter also referred to as "soot model") in the oil to be evaluated. This sooted candidate oil is spotted onto a strip of porous paper. The strip is developed in a chamber containing a solvent or solvent mix of a composition as described below. The mixture (mobile phase) is drawn up the strip by capillary action carrying with it the soot model. The extent to which the soot model moves up the strip correlates to soot dispersion.

Soot Model.

The soot model may be a commercially available carbon black. Examples are those in the Mogul® series of carbon blacks, available from Cabot Corporation. An example is Mogul-L® carbon black, which is advertised as an oxidized pigment black having a treated surface (i.e., chemically treated). Mogul-L® carbon black is believed to contain an O/C surface elemental ratio of 0.06 and a S/C surface elemental ratio of 0.01. This particular carbon black is also believed to contain a total surface acid concentration of 0.31 mmol/g and a surface carboxylic acid content of 0.18 mmol/g. Other commercially available soot models appropriate for use in the present test include, but are not limited to, BP™ 130, Raven™ 1040, and Eflex™ TP, from their various providers.

Mobile Phase.

Older tests made use of pure solvents such as pentane as the mobile phase in the above TLC evaluation. An aspect of the disclosed technology is that the current test makes use of a mixture of a major portion of a liquid hydrocarbon such as pentane with a minor portion of the oil formulation to be evaluated (not containing soot) or a related oil or oil formulation, as described in greater detail below. Such a mobile phase greatly increases the mobility of the soot model and directionally ranks test oils in the correct order.

Liquid Hydrocarbon.

The liquid hydrocarbon portion typically comprises a non-aromatic hydrocarbon that has a viscosity and a boiling point less than that of mineral oil, which is miscible with the oil formulation component. It will typically be a liquid at room temperature, e.g. 20-25° C. It may be a saturated hydrocarbon, and in some embodiments any amount of unsaturation that may be present will be sufficiently minor to have no practical effect on the chemical stability and non-reactivity of the hydrocarbon under test conditions. Thus, butane, which has a boiling point of around 0° C., would be permissible but often inconvenient because its use could require conditions of low temperature or increased pressure. At the other extreme, a higher molecular weight material or mixture such as kerosene or jet fuel (b.p. about 175-275° C.) may be used, although, due to its heavier nature, its mobility may be reduced and the test may therefore be less convenient. Particularly suitable materials include alkanes (non-cyclic) or cycloalkanes of 5 through 18 or 5 through 8 carbon atoms, such as pentane, hexane, or heptane, including various isomers thereof, branched or unbranched. Pentane, such as n-pentane or, alternatively, isopentane or mixed isomers thereof, is particularly convenient. The liquid hydrocarbon phase may also include mixtures of hydrocarbons such as, e.g., petroleum ether (b.p. 35-60° C.). Typical boiling points may thus include −10 to 175° C., or 0 to 175° C., or 25 to 125° C., or 30 to 100° C., or 30 to 85° C., or 30 to 40° C., or 60 to 85° C.

By way of comparison, the viscosity of a mineral oil, in particular a mineral oil of lubricating viscosity, expressed as kinematic viscosity, may be at least 2 or 3 or 4 or 5 or 6 or 9 $mm^2s^{-1}$ at 100° C. Thus the viscosity of the liquid hydrocarbon will be less than any one or more of these values. The boiling point of a mineral oil, in particular a mineral oil of lubricating viscosity, may often be expressed as a range, but will typically be or begin at least 300° C. or 370° C. or 400° C. under normal atmospheric pressure.

The amount of the hydrocarbon portion (or solvent) is a major amount of the chromatography mobile phase (also referred to as solvent mixture). Its amount may be 50 to 95 percent by weight, or 60 to 90 percent, or 70 to 85 percent, or 78 to 82 percent, or about 80 percent. The amount of the candidate oil in the chromatography solvent mixture is a minor amount, which may be 5 to 50 percent by weight, or 10 to 40 percent, or 15 to 30 percent, or 18 to 22 percent, or about 20 percent.

Optional Additional Component.

Beside the liquid hydrocarbon component, described above, and the oil component, described below, the mobile phase may optionally contain one or more additional solvents. These may include relatively more polar organic solvents which may include one or more heteroatoms and/or double bonds. Examples include ethyl acetate, chloroform, methylene chloride, and acetonitrile. The amount of such optional other component, in various embodiments, may be 0 to 10 percent of the mobile phase, or 0.1 to 5 percent, or 0.5 to 3 percent, or 1 to 2 percent by weight.

Oil Component.

The oil component or candidate oil, which is a portion of the chromatography mobile phase, may be a fully formulated lubricating oil (as described in greater detail below) and may typically be identical to, that is, of the same composition as, the oil sample (that is, the lubricating oil, or lubricant) in which the carbon black (or soot) is dispersed, except not containing the carbon black. In alternative embodiments, the candidate oil portion of the chromatography solvent may differ from the specific formulation in which the carbon black is suspended, particularly if the differences are those which are believed to have little or no effect on the dispersing performance. For instance, many engine lubricants contain a small amount of an antifoam agent, which is believed to have no effect on soot dispersion. The antifoam agent need not be included in the candidate oil portion. Changes in the presence, amount, or identity of other components may be made with discretion. For instance, the specific type or amount of antioxidant or overbased detergent or zinc dialkylthiophosphate may be varied. It is also possible, but generally not practical, to vary the amount or type of dispersant employed. It should be evident, however, that since the dispersant chemistry is reasonably directly pertinent to the question of soot dispersion, it would often be desirable that the dispersant component in the candidate oil portion of the chromatography solvent should be the same as or at least very similar to the dispersant component of the test sample containing the carbon black. For greatest convenience, in certain embodiments the candidate oil portion will be the same material as that in which the carbon black soot model is dispersed.

Preparing the Dispersion.

The samples to be examined may be prepared by dispersing carbon black "soot model" into a test fluid, typically an engine oil formulation. The amount of soot model will typically included in the test fluid in an amount of about 4.0 percent, e.g., 2 to 6 percent, 3 to 5 percent, or 3.5 to 4.5 percent, or 3.9 to 4.1 or 3.95 to 4.05, or even 3.98 to 4.02 percent by weight of the total test fluid. At low amounts, such as 2%, the soot spot which is obtained may be relatively light in color or intensity, making subsequent measurement more difficult. At higher concentrations, such as 6%, the soot may be relatively difficult to disperse in the sample.

The soot model may be dispersed within the test lubricant by any means providing sufficient agitation to effect dispersion. In certain embodiments, a Tissumizer™ homogenizer, that is, a high speed homogenizing device, may be effectively used. The homogenization may be conducted at any convenient temperature, such as room temperature (e.g., 20-25° C.).

The sample in which the soot model is dispersed will typically be a lubricant such as engine oil lubricant formulation, often a lubricant for a diesel engine. Diesel lubricants are known to be susceptible to soot contamination and, thus, soot dispersion is particularly beneficial for them.

Typical Lubricant Formulation.

A typical diesel lubricant may contain an oil of lubricating viscosity, including natural or synthetic lubricating oils and mixtures thereof. Natural oils include animal oils, vegetable oils, mineral lubricating oils of paraffinic, naphthenic, or mixed types, solvent or acid treated mineral oils, and oils derived from coal or shale. Synthetic lubricating oils include hydrocarbon oils, halo-substituted hydrocarbon oils, alkylene oxide polymers (including those made by polymerization of ethylene oxide or propylene oxide), esters of dicarboxylic acids and a variety of alcohols including polyols, esters of monocarboxylic acids and polyols, esters of phosphorus-containing acids, polymeric tetrahydrofurans, and silicon-based oils (including siloxane oils and silicate oils). Included are unrefined, refined, and rerefined oils and oils prepared by Fischer-Tropsch gas-to-liquid synthetic procedure as well as other gas-to-liquid oils. Specific examples of the oils of lubricating viscosity are described in U.S. Pat. No. 4,326,972. Oils of lubricating viscosity may also be selected from any of the base oils in Groups I-V as specified in the American Petroleum Institute (API) Base Oil Interchangeability Guidelines. The five base oil groups are as follows: Group I: >0.03% sulfur and/or <90% saturates and viscosity index 80 to 120; Group II: ≤0.03% S and ≥90% saturates and VI 80 to 120; Group III: ≤0.03% S and ≥90% saturates and VI >120; Group IV: all polyalphaolefins; Group V: all others. Groups I, II and III are mineral oil base stocks. In certain embodiments the oil is Group I or Group II.

The lubricating oil in a diesel lubricant will normally comprise the major amount of the composition. Thus it will normally be at least 50% by weight of the composition, such as 83 to 98%, or 88 to 90%.

Another common component in a diesel lubricant is a viscosity modifier. Viscosity modifiers (VM) and dispersant viscosity modifiers (DVM) are well known. Examples of VMs and DVMs include polymethacrylates, polyacrylates, polyolefins, hydrogenated vinyl aromatic-diene copolymers (e.g., styrene-butadiene, styrene-isoprene), styrene-maleic ester copolymers, and similar polymeric substances including homopolymers, copolymers, and graft copolymers. The DVM may comprise a nitrogen-containing methacrylate polymer, for example, a nitrogen-containing methacrylate polymer derived from methyl methacrylate and dimethylaminopropyl amine. The VMs and/or DVMs may be used in the functional fluid at a concentration of up to 20% by weight. Concentrations of 1 to 12% or 3 to 10% by weight may be used.

Also included may be an overbased detergent. Overbased materials, otherwise referred to as overbased or superbased salts, are generally single phase, homogeneous Newtonian systems characterized by a metal content in excess of that which would be present for neutralization according to the stoichiometry of the metal and the particular acidic organic compound reacted with the metal. The overbased materials are prepared by reacting an acidic material (typically an inorganic acid or lower carboxylic acid, preferably carbon dioxide) with a mixture comprising an acidic organic compound, a reaction medium comprising at least one inert, organic solvent (e.g., mineral oil) for said acidic organic material, a stoichiometric excess of a metal base such as Ca, Mg, or Na oxide or hydroxide, and a promoter such as a phenol or alcohol. The acidic organic material will normally have a sufficient number of carbon atoms to provide a degree of solubility in oil. The amount of excess metal is commonly expressed in terms of metal ratio. The term "metal ratio" is the ratio of the total equivalents of the metal to the equivalents of the acidic organic compound. A neutral metal salt has a metal ratio of one. A salt having 4.5 times as much metal as present in a normal salt will have metal excess of 3.5 equivalents, or a ratio of 4.5. Such overbased materials are well known to those skilled in the art. Patents describing techniques for making basic salts of sulfonic acids, carboxylic acids, phenols, phosphonic acids, and mixtures of any two or more of these include U.S. Pat. Nos. 2,501,731; 2,616,905; 2,616,911; 2,616,925; 2,777,874; 3,256,186; 3,384,585; 3,365,396; 3,320,162; 3,318,809; 3,488,284; and 3,629,109. Other overbased detergents include salixarate detergents, as described in U.S. Pat. No. 6,200,936.

Another component may be an antioxidant. Antioxidants encompass phenolic antioxidants, which may be hindered phenolic antioxidants, one or both ortho positions on a phenolic ring being occupied by bulky groups such as t-butyl. The para position may also be occupied by a hydrocarbyl group or a group bridging two aromatic rings. In certain embodiments the para position is occupied by an ester-containing group. Such antioxidants are described in greater detail in U.S. Pat. No. 6,559,105.

Antioxidants also include aromatic amines. In one embodiment, an aromatic amine antioxidant can comprise an alkylated diphenylamine such as nonylated diphenylamine or a mixture of a di-nonylated and a mono-nonylated diphenylamine. Antioxidants also include sulfurized olefins such as mono- or disulfides or mixtures thereof. Molybdenum compounds can also serve as antioxidants, and these materials can also serve in various other functions, such as antiwear agents or friction modifiers. U.S. Pat. No. 4,285,822 discloses lubricating oil compositions containing a molybdenum- and sulfur-containing composition.

Typical amounts of antioxidants will, of course, depend on the specific antioxidant and its individual effectiveness, but illustrative total amounts can be 0.01 to 5 percent by weight or 0.15 to 4.5 or 0.2 to 4 percent.

Yet another component may be a metal salt of a phosphorus acid. Metal salts of the formula

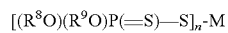

where $R^8$ and $R^9$ are independently hydrocarbyl groups containing 3 to 30 carbon atoms, are readily obtainable by heating phosphorus pentasulfide ($P_2S_5$) and an alcohol or phenol to form an O,O-dihydrocarbyl phosphorodithioic acid. The alcohol which reacts to provide the $R^8$ and $R^9$ groups may be a mixture of alcohols, for instance, a mixture of isopropanol and 4-methyl-2-pentanol, and in some embodiments a mixture of a secondary alcohol and a primary alcohol, such as isopropanol and 2-ethylhexanol. The resulting acid may be reacted with a basic metal compound to form the salt. The metal M, having a valence n, generally is aluminum, tin, manganese, cobalt, nickel, zinc, or copper, and in many cases, zinc, to form zinc dialkyldithiophosphates. Such materials are well known and readily available to those skilled in the art of lubricant formulation. Suitable variations to provide good phosphorus retention in an engine are disclosed, for instance, in US published application 2008-0015129, see claims.

A diesel lubricant will normally also contain a dispersant, designed to disperse soot and other components and products of combustion or oil degradation. The soot dispersion test described herein is designed, in large part, to evaluate the efficacy of a particular dispersant or mixture of dispersants in dispersing soot. Dispersants are well known in the field of lubricants and include primarily what is known as ashless dispersants and polymeric dispersants. Ashless dispersants are so-called because, as supplied, they do not contain metal and thus do not normally contribute to sulfated ash when added to a lubricant. However they may, of course, interact with ambient metals once they are added to a lubricant which includes metal-containing species. Ashless dispersants are characterized by a polar group attached to a relatively high molecular weight hydrocarbon chain. Typical ashless dispersants include N-substituted long chain alkenyl succinimides, having a variety of chemical structures including typically

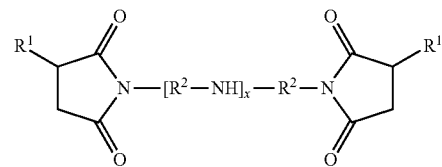

where each $R^1$ is independently an alkyl group, frequently a polyisobutylene group with a molecular weight ($M_n$) of 500-5000 based on the polyisobutylene precursor, and $R^2$ are alkylene groups, commonly ethylene ($C_2H_4$) groups. Such molecules are commonly derived from reaction of an alkenyl acylating agent with a polyamine, and a wide variety of linkages between the two moieties is possible beside the simple imide structure shown above, including a variety of amides and quaternary ammonium salts. In the above structure, the amine portion is shown as an alkylene polyamine, although other aliphatic and aromatic mono- and polyamines may also be used. Also, a variety of modes of linkage of the $R^1$ groups onto the imide structure are possible, including various cyclic linkages. The ratio of the carbonyl groups of the acylating agent to the nitrogen atoms of the amine may be 1:0.5 to 1:3, and in other instances 1:1 to 1:2.75 or 1:1.5 to 1:2.5. Succinimide dispersants are more fully described in U.S. Pat. Nos. 4,234,435 and 3,172,892 and in EP 0355895.

Another class of ashless dispersant is high molecular weight esters. These materials are similar to the above-described succinimides except that they may be seen as having been prepared by reaction of a hydrocarbyl acylating agent and a polyhydric aliphatic alcohol such as glycerol, pentaerythritol, or sorbitol. Such materials are described in more detail in U.S. Pat. No. 3,381,022.

Another class of ashless dispersant is Mannich bases. These are materials which are formed by the condensation of a higher molecular weight, alkyl substituted phenol, an alkylene polyamine, and an aldehyde such as formaldehyde and are described in more detail in U.S. Pat. No. 3,634,515.

Other dispersants include polymeric dispersant additives, which are generally hydrocarbon-based polymers which contain polar functionality to impart dispersancy characteristics to the polymer.

Dispersants can also be post-treated by reaction with any of a variety of agents. Among these are urea, thiourea, dimercaptothiadiazoles, carbon disulfide, aldehydes, ketones, carboxylic acids, hydrocarbon-substituted succinic anhydrides, nitriles, epoxides, boron compounds, and phosphorus compounds. References detailing such treatment are listed in U.S. Pat. No. 4,654,403.

The amount of the dispersant in a fully formulated engine (e.g., diesel) lubricant may be at least 0.1% of the lubricant composition, or at least 0.3% or 0.5% or 1%, and in certain embodiments at most 9% or 8% or 6% or 4% or 3% or 2% by weight.

Yet other components that may be present include pour point depressants, antifoam agents, corrosion inhibitors, rust inhibitors Pre-Stressing.

In one embodiment, the test lubricant in which the soot model is dispersed is pre-stressed at the time of or after incorporation of the soot model. That is, the test lubricant may be treated with a solution of water and acid, as one example, distilled or deionized water (45 parts by weight) containing concentrated sulfuric acid (45 parts) and concentrated nitric acid (10 parts). (The lubricant component of the mobile phase for the chromatography would typically not be pre-stressed in this way.) The relative amounts of water, concentrated sulfuric acid, and nitric acid may vary within the ratios as shown in the table below:

| water | sulfuric acid | nitric acid |
|---|---|---|
| 10-95 (provided at least 5% acid) | 0-90 | 0-90 |
| 20-80 | 16-65 | 4-15 |
| 30-65 | 29-57 | 6-13 |
| 40-50 | 41-49 | 9-11 |
| 43-47 | 43-47 | 10 |
| 45 | 45 | 10 |

The final normality of the acid solution may be 5 to 25 N, or 10 to 20 N, or 15 to 19 N or 17 to 18 N, e.g., 17.4 N. Enough of the acid solution is typically added to neutralize 12 TBN (total base number) equivalents of base present in the test lubricant containing the soot model, or alternatively 6 to 18 TBN or 8 to 16 or 12 to 13 TBN. Typically this may involve addition of 50 to 200 µL, or 100 to 150, or 110 to 125 µL of acid solution to a 10 g sample containing the lubricant and soot model. In a typical procedure, this mixture may be subjected to homogenization by the Tissumizer for about 1 minute to effect the homogenization and to at least begin the chemical pre-stressing process. The homogenized, soot model-containing sample may be maintained at elevated temperature, such as 90 to 100° C. (e.g., 93° C.) for 1 to 3 hours (e.g., about 2 hours) prior to chromatographic evaluation.

Chromatographic Evaluation.

In order to perform the chromatographic evaluation, a planar chromatography medium such as a strip of chromatography paper or a thin layer chromatography plate is spotted near one end with a small amount (e.g., 5 to 25 or 10 to 20 or about 15 µL) of the test fluid containing the soot model. The chromatography medium may be of any convenient size, including paper strips 16 to 18 mm wide and 165 to 170 mm long. The location of the spot may be 25 mm from one end of the strip. The spot should be permitted to adequately soak into the strip or other medium, e.g., over the course of 5 to 30 minutes, prior to proceeding with the chromatography.

Conducting a paper chromatographic analysis is a well-known technique, well within the capabilities of the person skilled in the art. The following is an example of how this may be conducted. The spotted chromatograph strip may be developed in an appropriate vessel in which the strip may be maintained in a roughly vertical position. For strips 17 mm×165 mm, a test tube of dimensions 40 mm×200 mm may be suitable. The vessel will contain an appropriate amount of the mobile phase (which may contain a portion of the specific lubricant to be tested, as described above) to a depth to wet the bottom of the strip but not to reach the level of the test spot. The test strip may be left in the test tube (which may be stoppered) for a sufficient time for the front of the mobile phase (solvent front) to advance nearly the entire height of the paper strip, that is, nearly to the top but not to the very top of the paper. The mobile phase will carry a portion of the dispersion along with it. This procedure may require, for example, 15 minutes or 10 to 20 minutes. After this time, the strip will be removed and permitted to dry.

The fully developed chromatography strip is visually evaluated in terms of extent of soot model that has migrated up the chromatography medium. This evaluation may be quantified by scanning the developed strip with appropriate hardware and software (e.g. Adobe Photoshop™ software), to obtain a digitalized image of the strip. The image may then be compared with a standard digitalized grid, as is illustrated in FIG. 1. The residual spot, 1, appears at the bottom of the image. The streak of discoloration, 2, resulting from the migration of the soot model, is also shown. The density of the discoloration arising from the soot model appears along the length of the paper, 3. The density of discoloration may be evaluated electronically by superimposing a grid (which may be stored as a separate image file in the Photoshop™ software) as shown in FIG. 1. Density may be evaluated on a "gray scale" at each of the superimposed circles, of which one is labeled, 4. The centers of the circles may be separated by 10 mm vertically and are designed and arranged so as to be superimposable on the chromatography strip and on the portion of the strip through which the solvent front has migrated. A circle encompassing a completely white area may be rated as 0%, and a completely black area may be rated as 100%. An overall rating for a strip would be the sum of 20 measurements within 20 circles distributed as shown along the length of the strip. The chromatography strip shown in FIG. 1 represents very good performance in terms of soot dispersion; such a candidate may have a rating of 400-500 (out of a possible maximum 2000). Detailed numerical values may, of course, vary from setup to setup, but within a given set of apparatus and test conditions, a high degree of consistency can be obtained.

The amount of each chemical component described herein is presented exclusive of any solvent or diluent oil, which may be customarily present in the commercial material, that is, on an active chemical basis, unless otherwise indicated. However, unless otherwise indicated, each chemical or composition referred to herein should be interpreted as being a commercial grade material which may contain the isomers, by-products, derivatives, and other such materials which are normally understood to be present in the commercial grade.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include: hydrocarbon substituents, including aliphatic, alicyclic, and aromatic substituents; substituted hydrocarbon substituents, that is, substituents containing non-hydrocarbon groups which, in the context of this invention, do not alter the predominantly hydrocarbon nature of the substituent; and hetero substituents, that is, substituents which similarly have a predominantly hydrocarbon character but contain other than carbon in a ring or chain. A more detailed definition of the term "hydrocarbyl substituent" or "hydrocarbyl group" is found in paragraphs [0137] to [0141] of published application US 2010-0197536.

EXAMPLES

Three API CH-4 15W-40 oils are prepared, representing "fair" (Lubricant Ex. 1), "good" (Lubricant Ex. 2), and "top-tier" (Lubricant Ex. 3) performance as evaluated in a Mack T-8E test. The T-8E test is a fired engine test of soot-mediated viscosity increase, defined in or based on ASTM D5967-11. This test, or a variation of it, is also described in U.S. Pat. No. 7,534,747, see column 13 lines 39-50. It is useful as a standard against which the present chromatographic test may be compared. An important parameter of the T-8E test is the viscosity increase of the lubricant at 3.8% soot loading, and the results are expressed in terms of cSt of kinematic viscosity at 100° C.

Each of the lubricants tested are 15W-40 viscosity grades containing olefin copolymer viscosity modifier, pour point depressant, overbased calcium detergents, succinimide dispersant, zinc dialkyldithiophosphate, sulfurized olefin and/or other antioxidants, and various other components. The detailed compositions of the lubricants differ, for example, in terms of the type and amount of dispersant, resulting in the difference in T-8E performance. For example, the "fair" and "good" lubricants are prepared in API Group I basestock while the "top-tier" lubricant is prepared in an API Group II basestock.

Evaluation of the example lubricants in the T8E test is shown in the following table:

| Lubricant Ex. | 1 | 2 | 3 |
|---|---|---|---|
| characterization | "fair" | "good" | "top-tier" |
| Mack T-8E viscosity increase at 3.8% soot (cSt, 100° C.) | 4.29 | 2.80 | 2.09 |

Each of the three lubricant examples is subjected to a series of "spot" tests. The first two represent known comparative or reference tests. The second two are variations within the scope of the disclosed technology.

Reference Test 1 (Pentane Mobile Phase)

A candidate oil (9.6 g) is added to a test tube along with Mogul-L™ carbon black (0.4 g). The mixture is agitated with a Tissumizer for 1 minute and then the sample is heated to 93° C. for 2 hours. The mixture, 15 μL, is blotted near the bottom of a strip of chromatography paper. The bottom end of the strip is submerged in a test tube in a mobile liquid phase consisting of pentane. The mobile phase moves up the chromatography paper by capillary action, moving (at least a portion of) the soot model with it. Once the strip is fully developed, it is removed from the test tube and allowed to dry. The dry strip is scanned on a flatbed scanner in gray scale mode. Twenty locations on the strip, on a standardized grid as described above, are rated for darkness, with a perfectly white location having a rating of 0 and a perfectly black location having a ratio of 100. The twenty numerical evaluations are summed. Each candidate oil is measured in duplicate or triplicate and the average values are reported.

Reference Test 2—Spot Test

A candidate oil is prepared as in Reference Test 1 and 25 μL is spotted onto chromatography paper. The paper is allowed to rest (not in solvent) for 2 hours at 90° C. During this time, the oil spreads out to a larger surface area of the paper, and the soot also spreads out, to a lesser extent. The ratio of the diameter of the outer oil spot to the inner soot spot is reported as a percentage, with high spot ratio ostensibly indicating better soot dispersion. Each candidate oil is measured in duplicate or triplicate and the average values are reported.

Inventive Technology: Test 3

The procedure of Reference Test 1 is followed except that the mobile phase for the chromatography is 80 weight percent pentane and 20 weight percent of the candidate oil being evaluated.

Inventive Technology: Test 4

The procedure of Inventive Technology Test 3 is followed except that a portion of the candidate oil (the portion to contain the soot model) is chemically pre-stressed with a solution of deionized water (27 parts by weight), concentrated sulfuric acid (27 parts by weight), and concentrated nitric acid (6 parts by weight). The normality of the acid solution is 17.4. The amount of the acid solution added is sufficient to neutralize 12 TBN equivalents of base, or an amount of about 118 μL of the acid solution.

The Table below shows the testing results for the oils with testing procedures 1 through 4. (Standard deviations a for the measurements, calculated from 2 or 3 runs, are provided in parentheses.)

| Lubricant Ex. | 1 | 2 | 3 |
|---|---|---|---|
| Characterization | "fair" | "good" | "top-tier" |
| Ref Test 1 (pentane): rating | 307 (23) | 270 (4) | 216 (26) |
| Ref Test 2 (spot test): spot ratio | 77 (1) | 75 (1) | 71 (1) |
| Inventive Test 3: rating | 436 (12) | 458 (28) | 496 (6) |
| Inventive Test 4: rating | 264 (70) | 474 (51) | 455 (52) |

Reference tests 1 and 2 actually rank the samples in the reverse order, with the "fair" sample (as determined by the T-8E test) scoring better than the "top-tier" sample.

Inventive test 3 directionally ranks the oils in the correct order with the good and top-tier oils outperforming the fair oil, and being ranked in the correct order. However, considering the standard deviations, the difference observed between the fair and the good oil may not be statistically significant.

Inventive test 4 shows the desired discrimination. Although the standard deviations are larger, the difference between the results from the fair oil and the good and top-tier oil is statistically significant. The good and top-tier oils give statistically similar results.

Each of the documents referred to above is incorporated herein by reference, including any prior applications, whether or not specifically listed above, from which priority is claimed. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as modified by the word "about." It is to be understood that the upper and lower amount, range, and ratio limits set forth herein may be independently combined. Similarly, the ranges and amounts for each element of the invention can be used together with ranges or amounts for any of the other elements. As used herein, the expression "consisting essentially of" permits the inclusion of substances that do not materially affect the basic and novel characteristics of the composition under consideration.

The invention claimed is:

1. A method for evaluating the dispersibility of soot in a lubricant formulation which comprises at least one dispersant, comprising the steps of:
   (a) preparing a dispersion of carbon black in the lubricant formulation;
   (b) depositing a sample of the dispersed carbon black from step (a) onto a planar chromatography medium;
   (c) subjecting the sample of (b) to chromatographic conditions comprising introducing a liquid mobile phase to one side of said sample and permitting the liquid mobile phase to migrate past the sample of (b), thereby causing at least a portion of said carbon black to migrate in the direction of the migration of the liquid mobile phase; and
   (d) evaluating the extent of migration of said carbon black by comparing the density of darkening due to carbon black at pre-defined locations along the chromatography medium;
   wherein said liquid mobile phase comprises a mixture of:
   (i) a liquid hydrocarbon portion comprising a hydrocarbon having viscosity and boiling point less than that of an oil of lubricating viscosity; and
   (ii) an oil component comprising an oil of lubricating viscosity and the dispersant or dispersants that are also contained within the lubricant formulation.

2. The method of claim 1 wherein the oil component of the liquid mobile phase is a separate portion of the lubricant formulation in which the carbon black is separately dispersed in step (a).

3. The method of claim 1 wherein the dispersion of the carbon black in the lubricant formulation is chemically pre-stressed by reaction with an acid.

4. The method of claim 3 wherein the acid comprises a mixture of sulfuric acid and nitric acid.

5. The method of claim 1 wherein the carbon black comprises particles of an oxidized pigment black having a chemically treated surface.

6. The method of claim 1 wherein the carbon black is dispersed within the lubricant formulation in an amount of substantially 2 to substantially 6 percent.

7. The method of claim 1 wherein the carbon black is dispersed within the lubricant formulation in an amount of substantially 3.95 to substantially 4.05 percent by weight.

8. The method of claim 1 wherein the amount of the carbon black-containing dispersion that is deposited onto the chromatography medium is about substantially 5 µL to substantially 25 µL.

9. The method of claim 1 wherein the amount of the carbon black-containing dispersion that is deposited onto the chromatography medium is substantially 15 µL.

10. The method of claim 1 wherein the oil component of the liquid mobile phase is a fully formulated diesel lubricant.

11. The method of claim 1 wherein the oil component of the liquid mobile phase is identical to the oil sample in which the carbon black is dispersed.

12. The method of claim 1 wherein the liquid hydrocarbon portion (i) of the mobile phase comprises a non-aromatic hydrocarbon.

13. The method of claim 1 wherein the liquid hydrocarbon portion (i) of the mobile phase comprises an alkane having 5 to 18 carbon atoms.

14. The method of claim 1 wherein the liquid hydrocarbon portion (i) of the mobile phase comprises an alkane having 5 to 8 carbon atoms.

15. The method of claim 1 wherein the mobile phase further comprises (iii) one or more additional solvents which may include one or more heteroatoms and/or double bonds.

16. The method of claim 1 wherein the planar chromatography medium comprises chromatography paper.

* * * * *